US008252000B2

(12) United States Patent
Zhou

(10) Patent No.: US 8,252,000 B2
(45) Date of Patent: Aug. 28, 2012

(54) FEMORAL CONDYLE CUTTING AND SHAPING DEVICE

(75) Inventor: Ximing Zhou, Beijing (CN)

(73) Assignee: Beijing Montagne Medical Device, Co. Ltd., Beijing (CN)

( * ) Notice: Subject to any disclaimer, the term of this patent is extended or adjusted under 35 U.S.C. 154(b) by 164 days.

(21) Appl. No.: 12/864,158

(22) PCT Filed: Jan. 28, 2008

(86) PCT No.: PCT/CN2008/000198
§ 371 (c)(1), (2), (4) Date: Jul. 22, 2010

(87) PCT Pub. No.: WO2009/094808
PCT Pub. Date: Aug. 6, 2009

(65) Prior Publication Data
US 2010/0292702 A1   Nov. 18, 2010

(51) Int. Cl.
*A61B 17/32* (2006.01)
(52) U.S. Cl. .......... 606/88; 606/79; 606/80; 606/82; 606/86 R; 606/89; 408/46
(58) Field of Classification Search .......... 606/79, 606/80, 82, 84, 88, 89, 180, 183; 408/25, 408/26, 76, 46, 48, 53
See application file for complete search history.

(56) References Cited

U.S. PATENT DOCUMENTS

| 5,228,459 | A |   | 7/1993 | Caspari et al. |  |
|---|---|---|---|---|---|
| 5,336,025 | A | * | 8/1994 | Ozawa et al. | 408/46 |
| 6,601,305 | B1 | * | 8/2003 | Fukuoka | 30/376 |
| 6,695,848 | B2 |   | 2/2004 | Haines |  |
| 7,641,662 | B2 | * | 1/2010 | Zhou | 606/88 |
| 2003/0235477 | A1 | * | 12/2003 | Schulz | 408/48 |
| 2007/0123899 | A1 | * | 5/2007 | Zhou | 606/88 |

FOREIGN PATENT DOCUMENTS

| CN | 1908463 A | 2/2007 |
|---|---|---|
| CN | 2875337 Y | 3/2007 |
| CN | 2936174 Y | 8/2007 |
| EP | 1543784 A2 | 6/2005 |
| JP | 200308833 A | 11/2000 |
| JP | 2002306500 | 10/2002 |
| WO | 03070111 A2 | 8/2003 |

OTHER PUBLICATIONS

International Search Report and Written Opinion issued in connection with Applicant's related International Patent Application No. PCT/CN2008/000198 entitled "Femoral Condyle Cutting and Shaping Device" (10 pages), Sep. 1, 2010.

* cited by examiner

*Primary Examiner* — Lorraine Spector
*Assistant Examiner* — Eric S Gibson
(74) *Attorney, Agent, or Firm* — Greenberg Traurig, LLP

(57) ABSTRACT

A femoral condyle cutting and shaping device includes a first bone shaping and cutting tool and at least one assistant shaft which are mounted in a sliding gearbox; at least one driven shaft mounted in a sliding gearbox; a first connecting member and a second connecting member, with one end of the first connecting member joining with one end of the second connecting member so as to form a hinge fitting; at least one other bone shaping and cutting tool mounted on the relevant driven shaft; an adjusting mechanism, which is connected with one driven shaft to change the relative position between the first bone shaping and cutting tool and the at least one other bone shaping and cutting tool. A bone shaping and cutting tool is also disclosed, which has flat or helical structure.

23 Claims, 21 Drawing Sheets

United States Patent US 8,252,000 B2

FEMORAL CONDYLE CUTTING AND SHAPING DEVICE

CROSS-REFERENCE TO RELATED APPLICATIONS

This application is a §371 national phase application of and claims priority to International Patent Application No. PCT/CN2008/000198 filed Jan. 28, 2008, the disclosure of which is incorporated herein by reference in its entirety for all purposes.

FIELD OF THE INVENTION

The present invention relates to a femoral condyle cutting and shaping device, particularly to a cutting device for shaping a femoral condyle by a single-time operation in which relative positional dimensions between bone shaping and cutting tools can be adjusted. During operation, said cutting device for shaping a femoral condyle is mounted to a knee condyle by means of a fixing device and operated to cut the femoral condyle of a human body into a desired shape having a plurality of required surfaces at the same time by sawing, milling, tiling or grinding.

BACKGROUND OF THE INVENTION

In some special cases, when an artificial component is needed to be fitted at a knee joint of a human body, the femoral condyle must be cut and shaped such that the femoral condyle will have a special dimension and shape to cooperate with a corresponding artificial component.

At present, in the operation of Total Knee Arthroplasty, it tends to take a very long time for an orthopedic surgeon to assure that the knee joint is well fitted and balanced. A proper ligament tension can be achieved when the balanced knee joint has a correct desired angle between the mechanical axis and the anatomic axis of the knee. This is very important for the entire motion of the knee joint. Thus, a more natural and effective artificial component of the knee joint and the wear resistance characteristics of the artificial component can be provided. The correct dimensions of the artificial component are also a very important factor, which will bring the operation into success or otherwise failure. If a wrong component is selected, or some dimension errors of the artificial component are formed, the associated soft tissue may become too tight or too loose, thus arousing a very poor usage performance of the artificial component.

An instrument for orthopedic surgical operation has been disclosed in a Chinese invention patent application disclosure CN1132067A, the application number of which Chinese invention patent application is 951190946 and the publication date of the same is Oct. 2, 1996. The orthopedic surgical instrument is used in the total knee arthroplasty to determine the dimension of a femur and respective implanted components and provide correct alignment indication and help a surgeon to achieve a proper soft tissue balance for the joint. The use of such an orthopedic surgical instrument can assist a surgeon in selecting dimensions of respective implanted components, determining the cutting amount of a bone on the distal end, providing a correct soft tissue balance and adjusting the instrument for cutting the bone. This known instrument provides a surgeon with several check and verification systems so that the surgeon can check whether the instrument has been correctly adjusted and the joint has been correctly balanced before cutting the femur. This orthopedic surgical instrument comprises a rotary alignment guide which assists a surgeon to determine correct rotary alignment of the knee joint. The correct rotary alignment of the knee joint is made by referring to standard boundary marks of a femur such as posterior condyle and superior condyle. This rotary alignment guide comprises a groove for guiding a saw blade which is used to remove the posterior condyle of the femur.

In summary, in the traditional art, the cutting operation for the femoral condyle is performed in steps, as shown in FIGS. 1-5. The first step is to perform osteotomy at the proximal tibia. Then, a guide is inserted into the femoral medulla, and the anterior portion of the femoral condyle is cut roughly, through which the angle of external rotation of the artificial femoral component can be determined. Subsequently, the osteotomy at the distal femur is performed to find out the valgus angle and the joint line. Then, the dimensions of the femoral component are calculated. After that, the osteotomy at the anterior and posterior condyles of the femur and the osteotomy at the anterior and posterior bevel angles of the femur are performed. The cruciate ligament and the meniscus are removed, and thereafter the flexion gap is measured by means of spacers and the correctness of the osteotomy of the tibia is determined, whether the extension gap is correct is determined by extending the knee, and the whole alignment and the balance status of ligaments are measured. If necessary, the osteotomy of the femur is further performed, the distal femur is repaired, the osteotomy in the intercondylar notch of the femur is performed, and the osteotomy in a bevel angle is performed. Thereafter, a plug hole for the artificial tibial component is chiseled, and the angle of external rotation of the artificial tibial component is determined. Then, the osteotomy of the patella is performed, a fixing hole for the artificial patellar component is bored, and the motion path of the patella is checked.

As shown in FIGS. 1-5, since this traditional method performs the osteotomy at five surfaces of the distal femur in steps, namely, the osteotomy at the front portion of the femoral condyle, the osteotomy at the distal femur, the osteotomy at the anterior and posterior condyles of the femur, and the osteotomy at the anterior and posterior bevel angles of the femur, the disadvantages are as follows: poor accuracies of the angles among the respective bone resected surfaces make it impossible to completely match the cut surfaces with the prosthesis; in addition, the operation scheme is complex, with a lot of operation instruments needed, and the operative process is hard to be controlled, resulting in a long time of the osteotomy. Such an operation often brings great pains to a patient, or even some accidental cases may occur due to a long time operation; a lot of complication diseases may be ensued if the prosthesis is not matched with the bone resected surfaces.

In a U.S. Pat. No. 7,641,662 (Jan. 5, 2010), a femoral condyle cutting and shaping center is provided for shaping a plurality of surfaces at the same time. However, this femoral condyle cutting and shaping center cannot adjust the distances among the respective cutting and shaping tools, so that it is impossible to adjust the cutting shapes and dimensions in the osteotomy according to different patents and achieve the anti-clockwise and clockwise rotatable cutting.

SUMMARY OF THE INVENTION

It is an object of the present invention to overcome the above-mentioned deficiencies in the prior art, by providing a femur cutting machine, i.e. a femoral condyle bone cutting and shaping device for the current artificial total knee arthroplasty, which is adjustable in dimensions and capable of clockwise or anti-clockwise cutting, which could complete the cutting and shaping in a single operation, and which is foolproof operative, economical, simple, accurate and inerrant. This femoral condyle cutting and shaping device is capable of incising from the intercondylar notch, cutting bidirectionally to the left side and the right side, and reducing soft tissue exposure, and therefore it helps to narrow the surgical incision and to prevent lateral collateral ligaments from injury. It assures an accurate and rapid bone cutting, guarantees an equal clearance for the knee joint at an extension position and a flexion position, and the balance of the lateral and medial soft tissues of the knee joint, so as to reduce the risk of negligence in operation, and improve the surgical level and quality.

It is an object of the present invention to provide a femoral condyle cutting and shaping device, which comprises: a first bone shaping and cutting tool, disposed on an extending end portion of a main driving shaft; and a fixed gearbox including the main driving shaft that is supported on the case of the fixed gearbox, a main driving gear being mounted on the main driving shaft. The femoral condyle cutting and shaping device further comprises: at least one assistant shaft mounted inside the case of the fixed gearbox, wherein said at least one assistant shaft has a respective assistant gear mounted thereon, and one of said at least one assistant gear which is adjacent to said main driving gear is mutually engaged with said main driving gear; a sliding gearbox including a sliding gearbox case which is capable of being guided to slide in the case of the fixed gearbox, wherein said sliding gearbox includes at least one driven shaft mounted on the case of the sliding gearbox and at least one driven gear mounted on said at least one driven shaft respectively, one of said at least one driven gear which is adjacent to said assistant gear is mutually engaged with said assistant gear, and the axes of said at least one driven shaft and said main driving shaft are parallel to each other; a first connecting member and a second connecting member, said assistant shaft being supported on the first connecting member, wherein said first connecting member is supported on said main driving shaft at one end of the first connecting member, the other end of said first connecting member is mounted together with one end of said second connecting member onto one of said at least one assistant shaft so as to form a pivotal connection, and the other end of said second connecting member is connected to one of said at least one driven shaft; at least one additional bone shaping and cutting tool, mounted on a portion of its corresponding driven shaft which extends outside the sliding gearbox case; an adjusting mechanism arranged outside the case of said fixed gearbox and connected to one of said at least one driven shaft so as to change the relative positions of said first bone shaping and cutting tool and said at least one additional bone shaping and cutting tool.

Preferably, said at least one assistant shaft comprises two assistant shafts, i.e. a first assistant shaft and a second assistant shaft, and wherein a first assistant gear on the first assistant shaft and a second assistant gear on the second assistant shaft are engaged with each other.

Preferably, said at least one driven shaft comprises two mutually engaged driven shafts, i.e. a first driven shaft and a third driven shaft.

Preferably, said at least one driven shaft comprises three driven shafts that engage one another, i.e. a first driven shaft, a second driven shaft and a third driven shaft.

Preferably, said adjusting mechanism has an adjusting mechanism body with an involute sliding groove formed thereon, and a connecting means that connects said adjusting mechanism with one of said at least one driven shaft and is slidable in the involute sliding groove.

Preferably, said adjusting mechanism body is provided with a guiding groove for a positioning pin, which is parallel to the sliding groove and has a plurality of positioning holes therein, and wherein said positioning holes cooperate with the positioning pin attached to the sliding gearbox case, so as to fix the respective bone shaping and cutting tools.

Preferably, said plurality of positioning holes have different depths.

Preferably, the adjusting mechanism body further includes a flat plate-shaped cam portion that engages with a recess on the main driving shaft.

Preferably, said adjusting mechanism comprises a screw disposed in an opening of the adjusting mechanism body and connected to the case of the fixed gearbox, and a compression spring surrounding said screw.

Preferably, said connecting means that connects said adjusting mechanism and said one driven shalt is a portion of said driven shaft, or a rod that is connected to said one driven shaft.

Preferably, two positioning guide plates are arranged on the two opposite sides of the case of said fixed gearbox, respectively, and each of said positioning guide plates is provided with a handle at an end thereof, and wherein a protective shield is also arranged on said fixed gearbox case to surround the first bone shaping and cutting tool, and another positioning guide plate is provided on said protective shield.

Preferably, said bone shaping and cutting tools comprises a plurality of blades each having a sheet-like structure, wherein each of the blades has a flat plate-shaped structure of constant thickness, or exhibits a conical shape having one or more tapers in the blade's width and/or thickness direction.

Preferably, the bone shaping and cutting tools each comprises a plurality of blades each having a helical structure, and wherein each of the blades has a helical plate-shaped structure of constant thickness, or has a helical structure that exhibits a conical shape having one or more tapers in the blade's width and/or thickness direction.

Preferably, the edge of each of the blades is provided with helical chip breakers or linear chip breakers formed in a direction perpendicular to an axial direction of the femoral condyle cutting and shaping device.

Preferably, the cutting edges of the blade are anti-clockwise cutting edges and/or clockwise cutting edges.

Preferably, said bone shaping and cutting tool is a single-blade cutting tool, and comprises a blade and three cutting edges formed on a shaft of the tool, a clearance being formed behind each of the cutting edges.

The femoral condyle cutting and shaping device as provided by the present invention is capable of reducing the time for performing the osteotomy upon the femoral condyle, capable of being positioned to complete shaping the femoral condyle at one time, attaining accurate orientations and accurate dimensions for cutting the condyle, such that the cutting surfaces of the femoral condyle are accurately matched with the prosthesis so as to simplify the surgical process, shorten the surgical time, alleviate the pain of a patient and improve the safety of the surgery.

The shape, dimensions and number of the bone shaping and cutting tools can be determined according to the prosthesis for the femoral condyle when using the femoral condyle cutting and shaping device according to the present invention.

In use of the femoral condyle cutting and shaping device according to the present invention during the surgery, the relative positional dimensions between the bone shaping and cutting tools of the femoral condyle cutting and shaping device can be adjusted according to the size of a femoral condyle so as to cut and shape the femoral condyle at the same time.

DETAILED DESCRIPTION OF THE DRAWINGS

Figure 1:
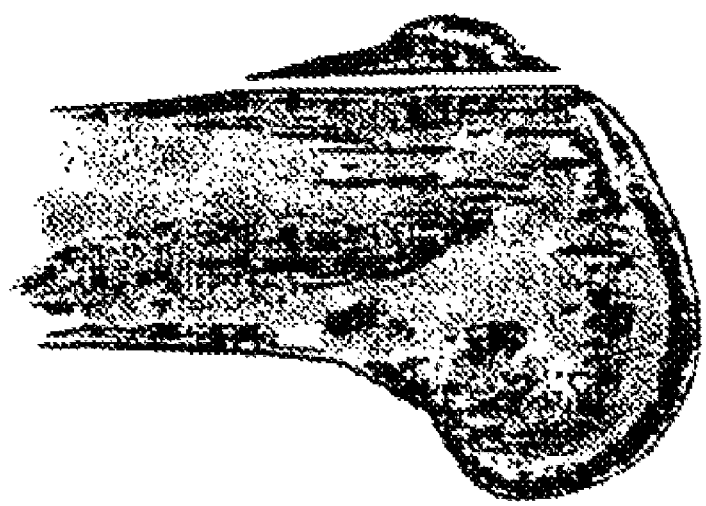
FIG. 1 is a schematic view of performing traditional osteotomy at a front portion of the femoral condyle.
Figure 2:
FIG. 2 is a schematic view of performing traditional osteotomy at a distal femur.
Figure 3:
FIG. 3 is a schematic view of performing traditional osteotomy at anterior and posterior condyles of a femur.
Figure 4:
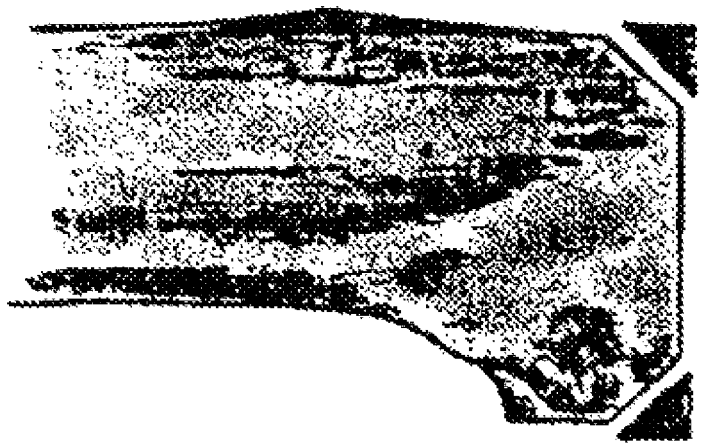
FIG. 4 is a schematic view of performing traditional osteotomy in a bevel angle and an intercondylar notch.
Figure 5:
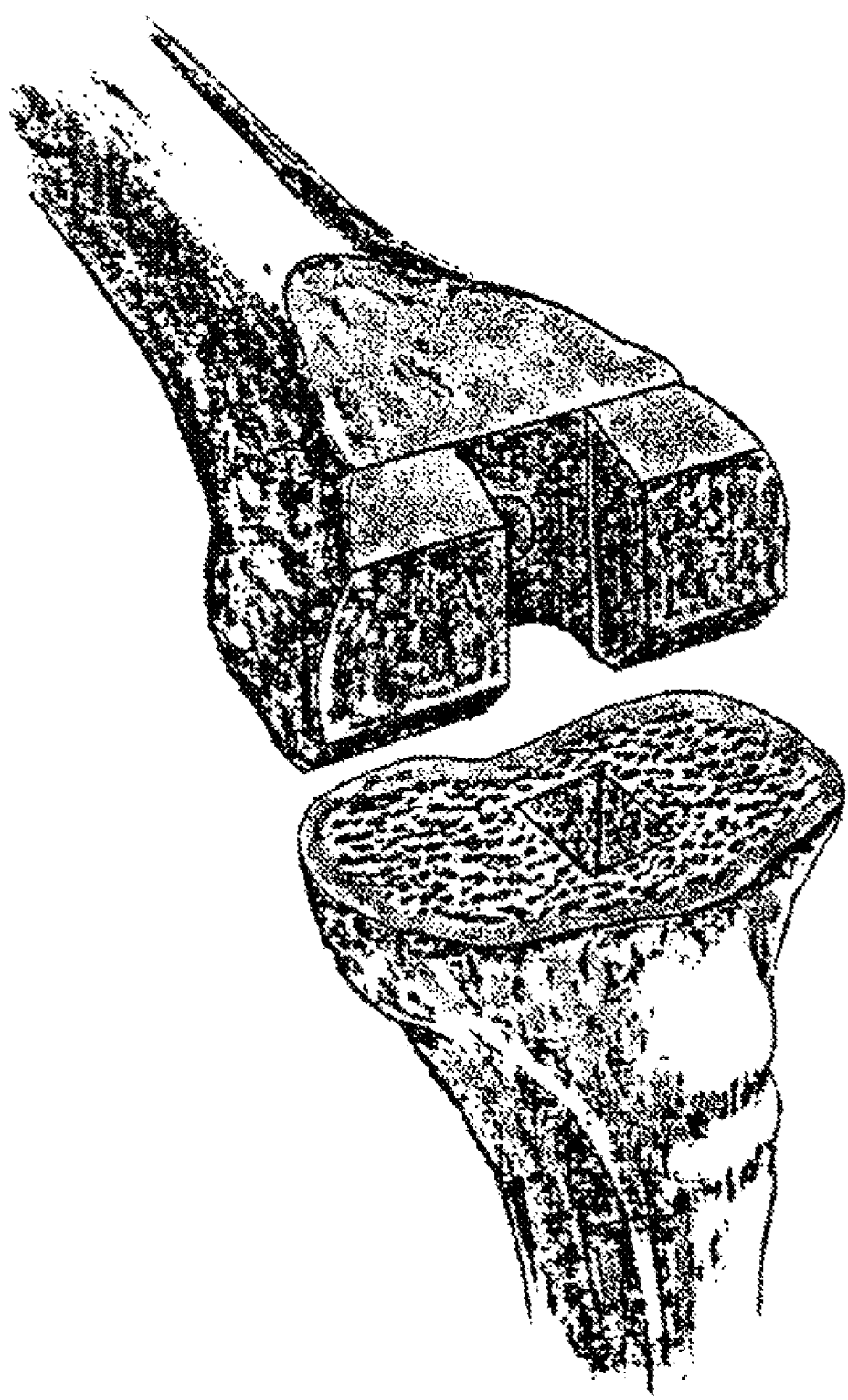
FIG. 5 is a schematic perspective view of a tibia and a femoral condyle after the cutting operation is finished.

A first preferred embodiment of a femoral condyle cutting and shaping device according to the present invention is described below in detail by referring to FIGS. 6-8C. In the embodiment shown in FIG. 6, the femoral condyle cutting and shaping device 10 of the present invention comprises a first assistant gear 2 that is mutually engaged with the main driving gear 1. A main driving shaft 3 is supported on a case 4 of a fixed gearbox. The first assistant gear 2 is mounted on a first assistant shaft 5 which is in turn supported on a first connecting member 6. One end of the first connecting member 6 is supported on the main driving shaft 3, and one end of the main driving shaft 3 extends outwardly of the fixed gearbox. A first bone shaping and cutting tool 11 is mounted on the extending end of the main driving shaft 3.

A second assistant gear 8 which is mounted on a second assistant gear shaft 7 and the first assistant gear 2 are mutually engaged. The second assistant shaft 7 is supported on a second connecting member 9, with one end of the second connecting member 9 being supported on a first driven shaft 15. The other end of the first connecting member 6 and the other end of the second connecting member 9 are connected to the second assistant shaft 7. The first driven shaft 15 is supported on a case 24 of the sliding gearbox which slides on the case 4 of the fixed gearbox by means of a guiding device (not shown). The first driven shaft 15 has a portion that extends outwardly of the case 24 of the sliding gearbox and a second bone shaping and cutting tool 12 is mounted on the outwardly extending portion of the first driven shaft 15.

A first driven gear 16 and a second driven gear 18 which is fixed on a second driven shaft 17 are mutually engaged. The second driven shaft 17 is supported on the case 24 of the sliding gearbox and has a portion that extends outwardly of the case 24 of the sliding gearbox. A third bone shaping and cutting tool 13 is mounted on the extending portion of the second driven shaft 17.

Figure 6:
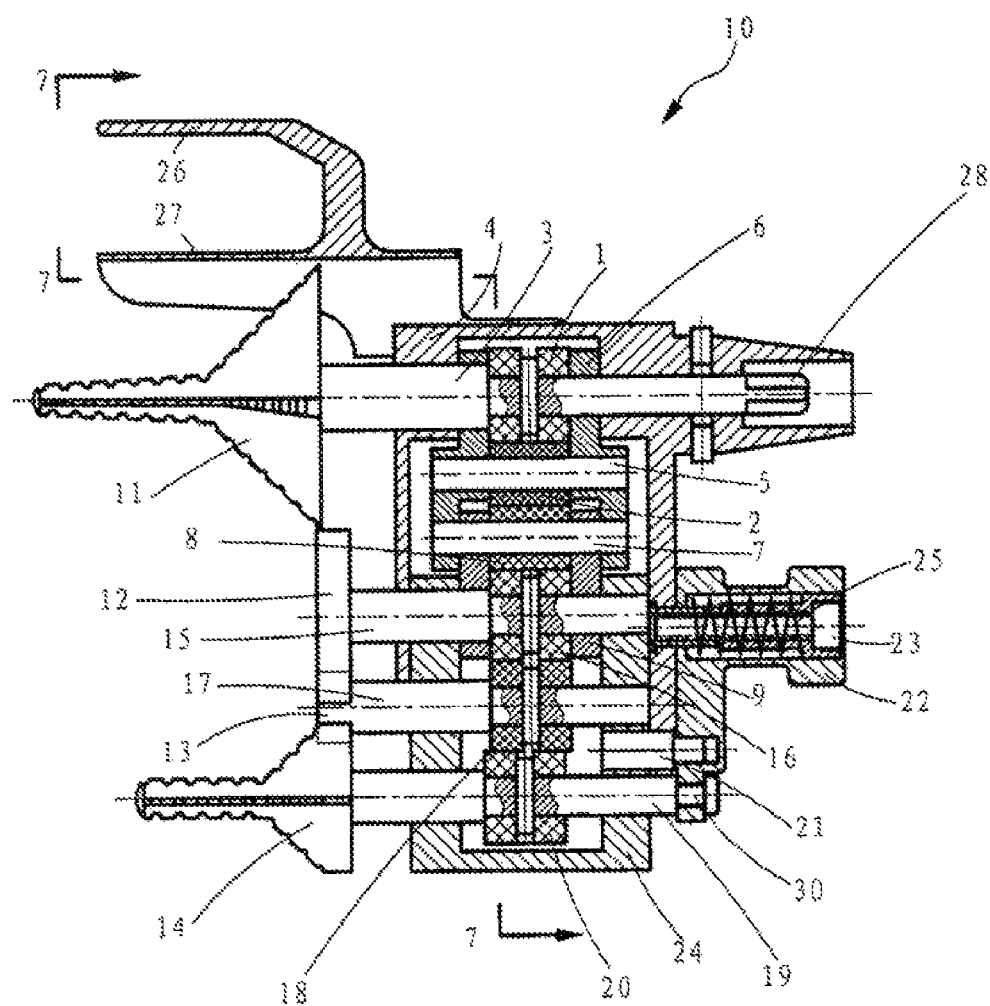
FIG. 6 is a longitudinal sectional view showing the first embodiment of a femoral condyle cutting and shaping device according to the present invention, wherein an adjusting mechanism is located at a fixed position.

As shown in FIG. 6, the second driven gear 18 and a third driven gear 20 which is fixed on a third driven shaft 19 are mutually engaged. The third driven shaft 19 is supported on the case 24 of the sliding gearbox. One end of the third driven shaft 19 has an outwardly extending portion on which a fourth shaping and cutting tool 14 is mounted. The other end of the third driven shaft 19 also has an outwardly extending portion on which a connecting means 30 is formed to be connected to a body 22 of an adjusting mechanism. The connecting means 30 may be formed by cutting a groove on the third driven shaft 19, or could be a component, such as a rod, which is connected to the third driven shaft 19.

Figure 7:
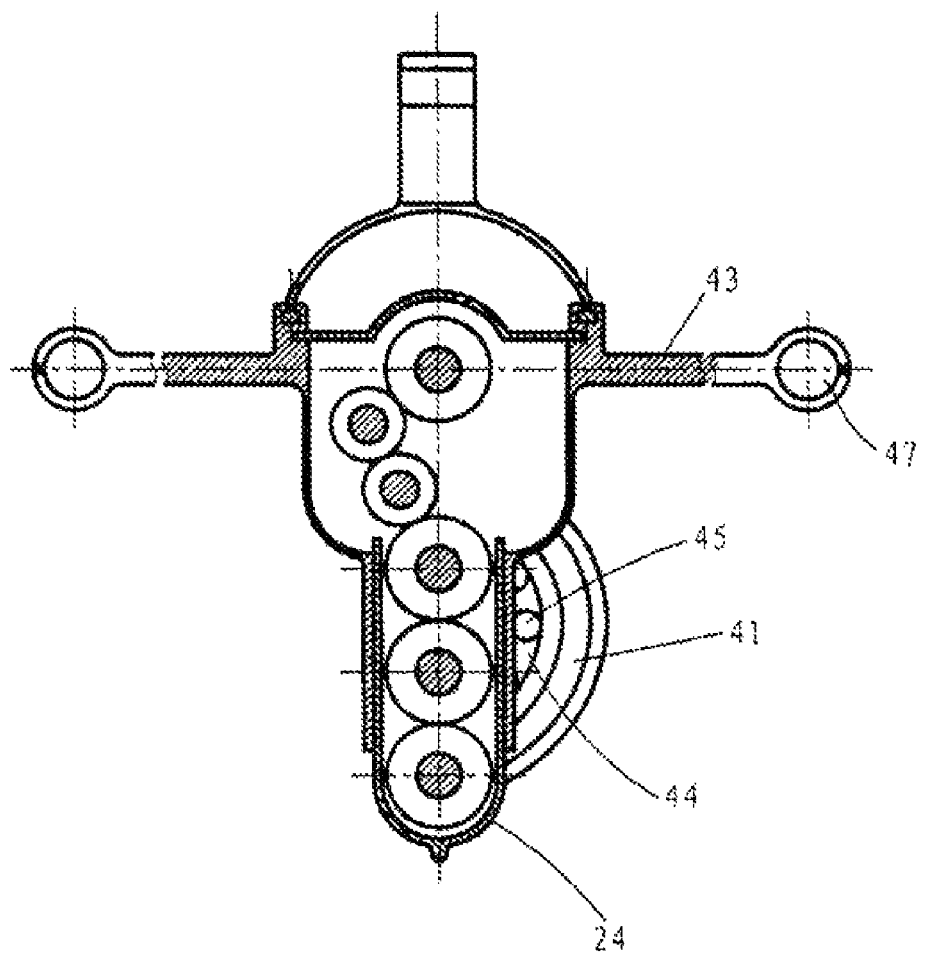
FIG. 7 is a side sectional view showing the first embodiment of a femoral condyle cutting and shaping device according to the present invention along the line 7-7 in FIG. 6.

As shown in FIGS. 6 and 7, the axes of the main driving shaft 3, the first driven shaft 15, the second driven shaft 17 and the third driven shaft 19 are parallel to each other. These axes as shown in FIG. 7 are located in a same plane, but a person skilled in the art can understand that these axes may be not located in a same plane. The positions of the axes of the first assistant shaft 5 and the second assistant shaft 7 can be changed by the adjustment of the adjusting mechanism.

Figure 8C:
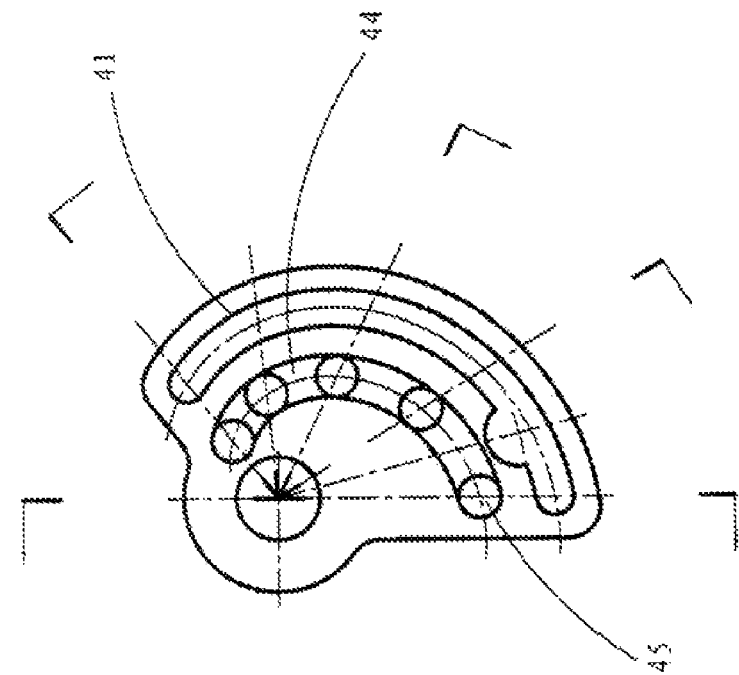
FIG. 8C is a left side view showing the adjusting mechanism in the first embodiment of the femoral condyle cutting and shaping device according to the present invention in FIG. 8A.
Figure 8A:
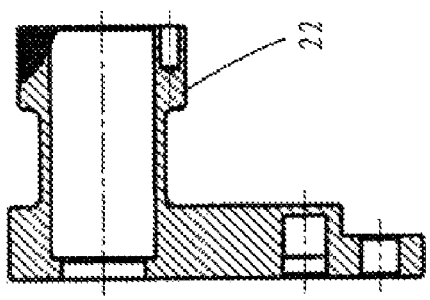
FIG. 8A is a longitudinal sectional view showing a body of an adjusting mechanism in the first embodiment of the femoral condyle cutting and shaping device according to the present invention.
Figure 8B:
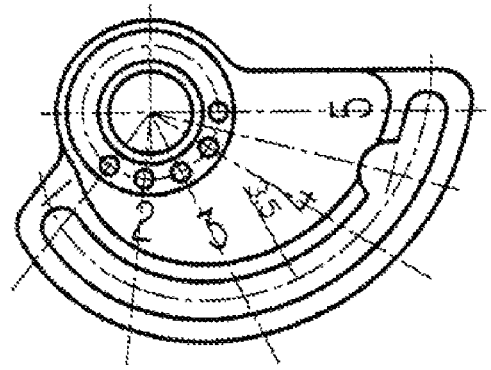
FIG. 8B is a right side view showing the adjusting mechanism in the first embodiment of the femoral condyle cutting and shaping device according to the present invention in FIG. 8A.

FIG. 8A is a longitudinal sectional view showing the body of a cam adjusting mechanism according to the present invention. FIG. 8B is a right side view of the cam adjusting mechanism according to the present invention. FIG. 8C is a left side view of the cam adjusting mechanism according to the present invention. As can be seen from these figures, a sliding groove 41 in the shape of an involute is arranged outermost on the cam of the adjusting mechanism body 22, and a positioning pin guiding groove 44 in the shape of an involute is provided on an inner side of the involute-shaped sliding groove 41, parallel to the sliding groove 41. There are five positioning holes provided in the positioning pin guiding groove 44 as shown in FIGS. 8A-8C. The intervals, the number and the depths of the positioning holes can be selected according to practical requirements.

As shown in FIG. 6, an adjusting mechanism is mounted outside the case 4 of the fixed gearbox. The adjusting mechanism comprises an adjusting mechanism body 22 that is supported on the case 4 of the fixed gearbox. A positioning pin 21 is inserted into one of the positioning hole 45 of the guiding groove 44 on the adjusting mechanism body 22, wherein the positioning holes may have the same or different depths. The positioning pin 21 is fixed to the case 24 of the sliding gearbox, and the adjusting mechanism body 22 is attached to the case 4 of the fixed gearbox by means of a screw 23 and a compression spring 25 around it. The sliding groove 41 on the adjusting mechanism body 22 is associated with the connecting means 30 provided on the extending portion of third driven shaft. The connecting means 30 may be slid in the sliding groove 41 so as to adjust the distances between the first bone shaping and cutting tool 11 and the second, third and fourth bone shaping and cutting tool 12, 13 and 14 in the case 24 of the sliding gearbox.

As shown in FIGS. 6 and 7, positioning guide plates 43 and protecting shields 27 surrounding the first bone shaping and cutting tool 11 are arranged on the two opposite sides of the case 4 of the fixed gearbox. Each of the guiding plates 43 is provided at an end thereof with a handle 47, and the protective shield 27 is further provided with another positioning guide plate 26. The main driving shaft 3 is provided with a coupling on one of its ends, which is a conical dynamic coupling 28 as shown in the FIG. 6.

In a practical operation, by fixing the positioning guide plates 43 at both sides of the fixed gearbox, the femoral condyle cutting and shaping device 10 is placed into a guiding groove of a femoral guiding device on the femoral condyle, to dynamically couple the main driving shaft 3 with the surgical power supply by means of the coupling 28. Then, by mutually engaging the main driving gear and the first assistant gear, the first assistant gear and the second assistant gear are mutually engaged, the second assistant gear is engaged with the first driven gear, the first driven gear is engaged with the second driven gear, and the second driven gear is engaged with the third driven gear, so as to rotate the first to the fourth bone shaping and cutting tools on the corresponding shafts, and to carry out the osteotomy by sliding the femoral condyle cutting and shaping device 10 left and right along the guiding groove of the femoral guiding device.

Figure 9:
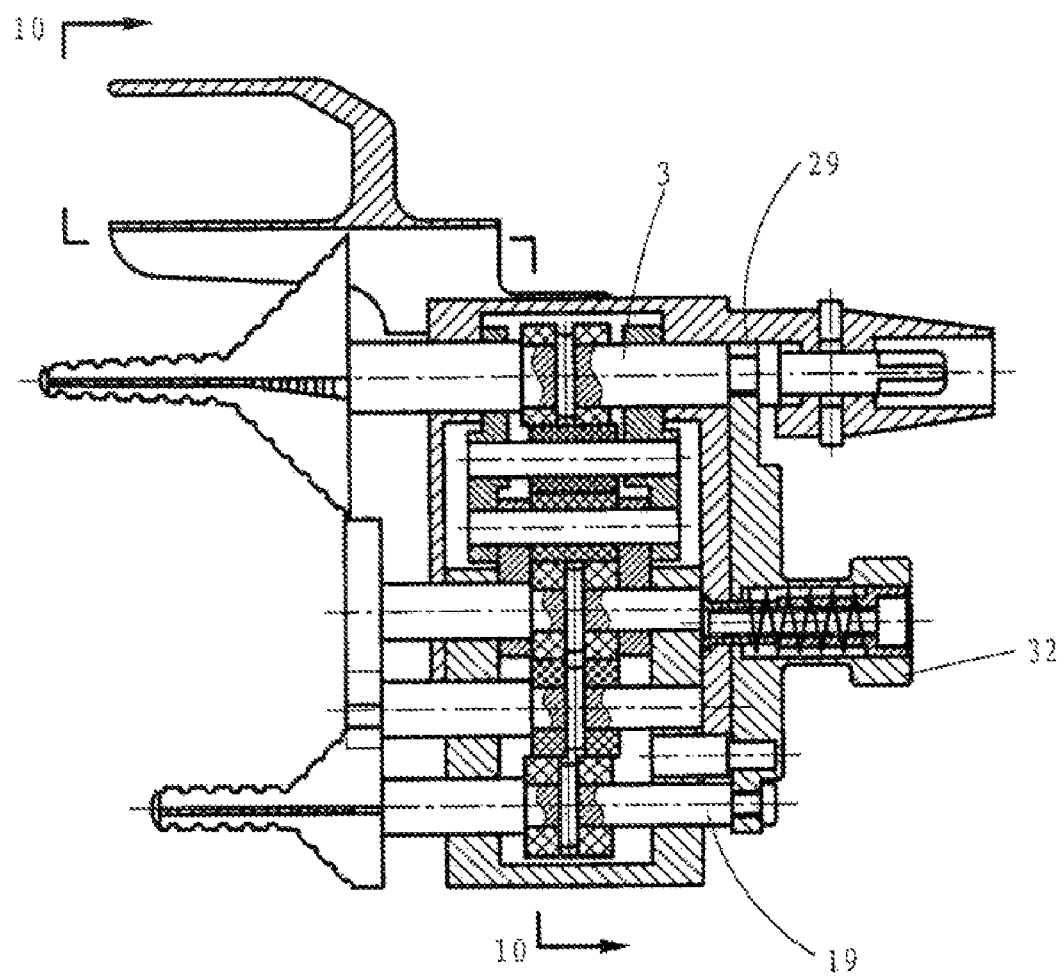
FIG. 9 is a longitudinal sectional view showing a second embodiment of a femoral condyle cutting and shaping device according to the present invention, wherein an adjusting mechanism is located at a fixed position.
Figure 10:
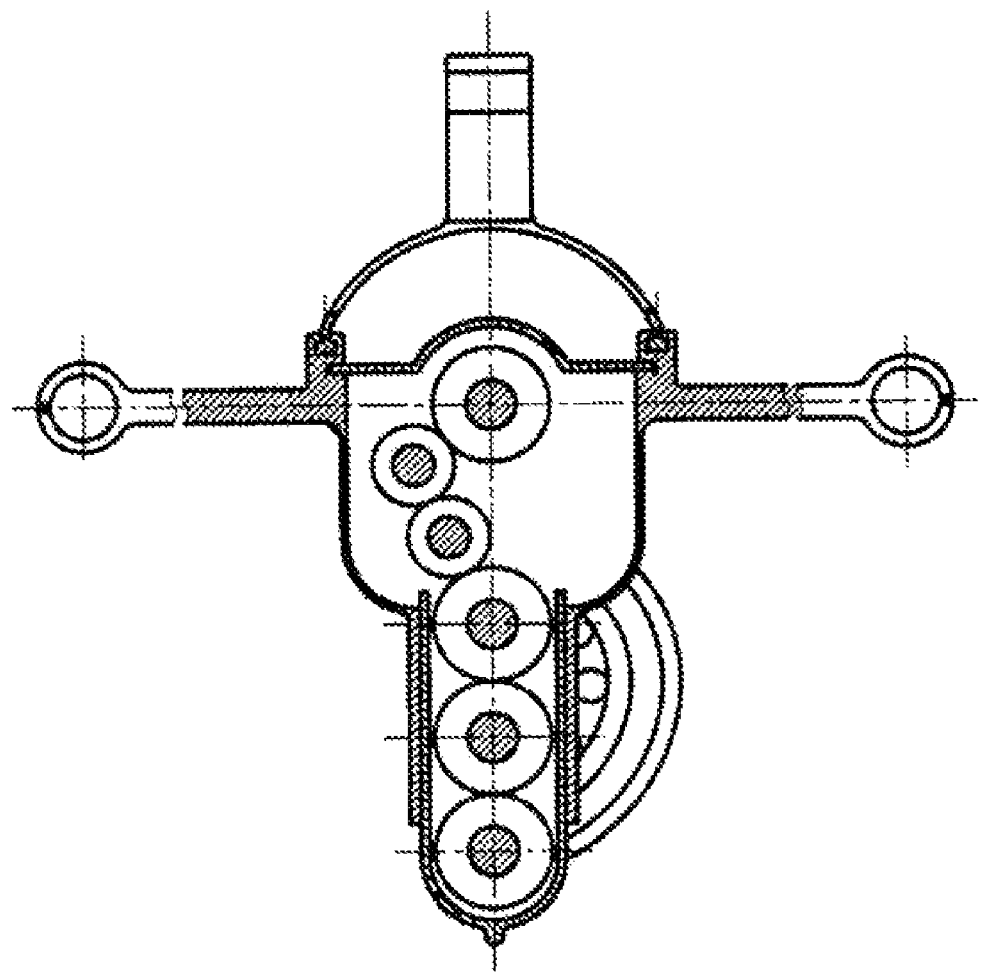
FIG. 10 is a side sectional view showing the second embodiment of the femoral condyle cutting and shaping device according to the present invention along the line 10-10 in FIG. 9.

FIG. 9 is a longitudinal sectional view showing the second embodiment of the femoral condyle cutting and shaping device according to the present invention. FIG. 10 is a side sectional view showing the second embodiment of the femoral condyle cutting and shaping device according to the present invention along the line 10-10 in FIG. 9. In the femoral condyle cutting and shaping device in FIGS. 9 and 10, the main driving shaft 3 is movable in the axial direction simultaneously with a body 32 of the adjusting mechanism and the third driven shaft 19. The second embodiment as shown in FIGS. 9-10 is substantially identical with the first embodiment as shown in FIGS. 6-7, except that a recess 29 is provided on the main driving shaft 3 so as to engage one end of the main body 32 of the adjusting mechanism into the recess 29. A flat plate-shaped cam part 46 of the body 32 of the adjusting mechanism is inserted into the recess 29.

Figure 11:
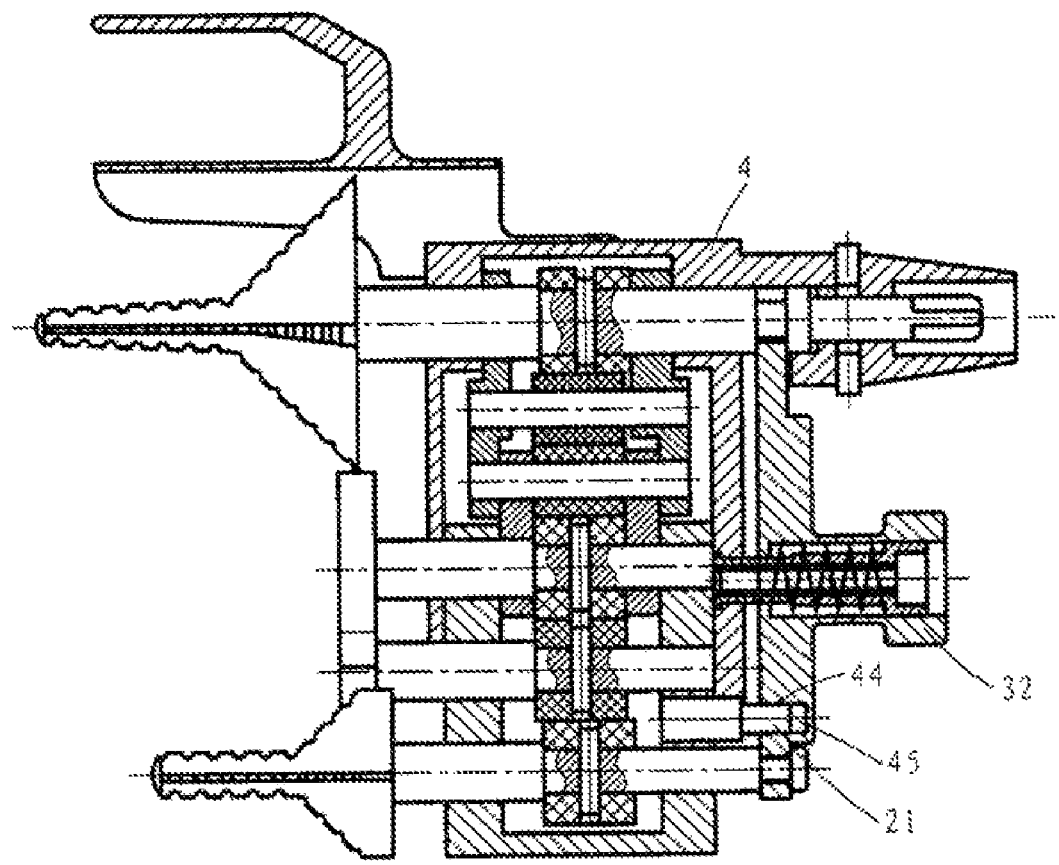
FIG. 11 is a longitudinal sectional view showing the second embodiment of the femoral condyle cutting and shaping device according to the present invention, wherein the adjusting mechanism is located at an adjusting position.

FIG. 11 is a longitudinal sectional view showing the second embodiment of the femoral condyle cutting and shaping device according to the present invention, wherein the adjusting mechanism body 32 is pulled away from the case 4 of the fixed gearbox by a distance. When the body 32 of the adjusting mechanism is axially pulled away, the main driving shaft 3 is driven to move axially along with the axial movement of the flat cam part 46 such that the first bone shaping and cutting tool 11 in the fixed gearbox can move axially. Meanwhile, the axial movement of the body 32 of the adjusting mechanism also drives the third driven shaft 19 to axially move. At this time, the positioning pin 21 is disengaged from the positioning hole 45 in the guiding groove 44 in the adjusting mechanism body, but still stays in the guiding groove 44. Then the adjustment mechanism body 32 is rotated to slide the positioning pin 21 along the guiding groove. When the poisoning pin is rotated by a certain angle to be aligned with another positioning hole 45, the body 32 of the adjusting mechanism is released, and the positioning pin 21 is inserted into said another positioning hole 45 under the bias of the compression spring 25. Due to the five positioning holes 45 of the different depths, the axial positions of the respective bone shaping and cutting tools are changed. Simultaneously, in this way, the adjustment upon the distances of the second, the third, the fourth bone shaping and cutting tools 12, 13 and 14 in the sliding gearbox with respect to the first bone shaping and cutting tool 11 in the fixed gearbox is finished.

Figure 12C:
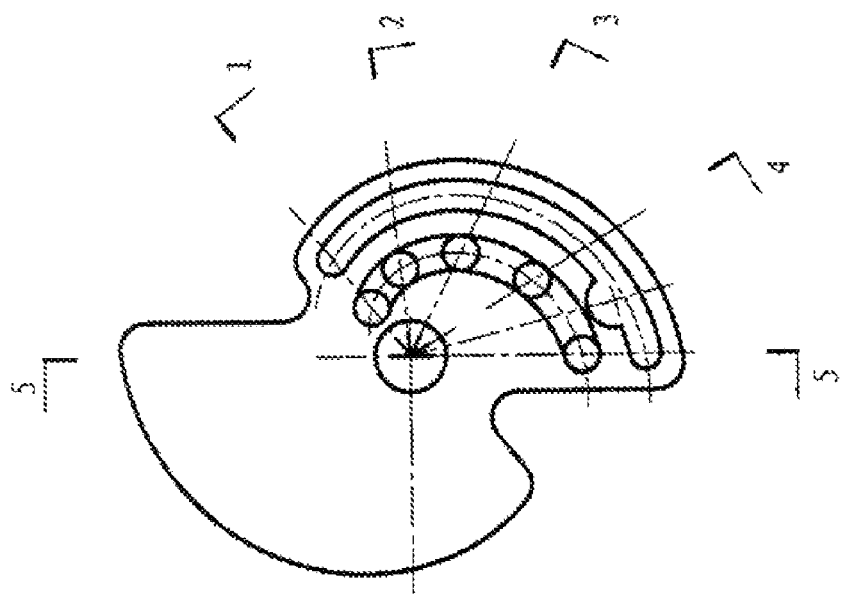
FIG. 12C is a left side view showing the adjusting mechanism body in the second embodiment of the femoral condyle cutting and shaping device according to the present invention in FIG. 12A.
Figure 12A:
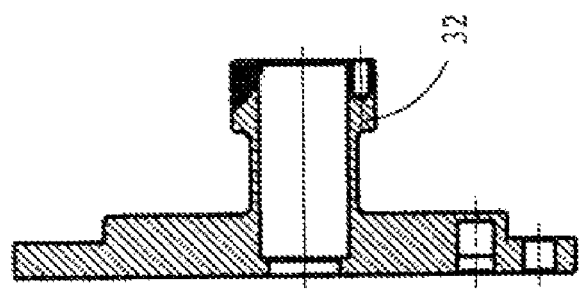
FIG. 12A is a longitudinal sectional view showing the adjusting mechanism body in the second embodiment of the femoral condyle cutting and shaping device according to the present invention.
Figure 12B:
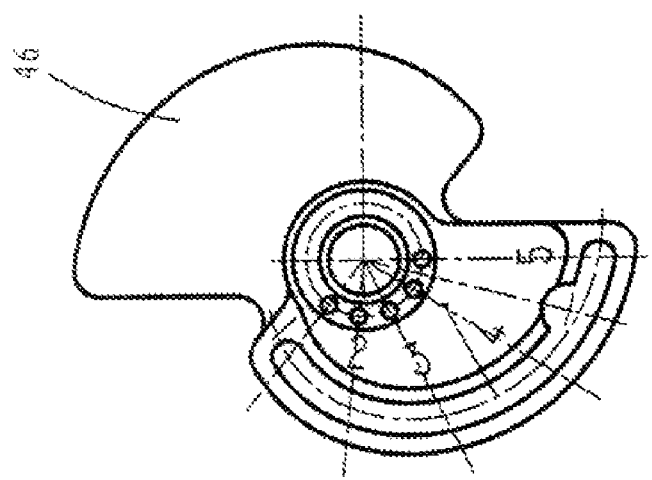
FIG. 12B is a right side view showing the adjusting mechanism body in the second embodiment of the femoral condyle cutting and shaping device according to the present invention in FIG. 12A.

The body of the adjusting mechanism of the cutting and shaping device is shown in FIGS. 12A-12C. The body of the adjusting mechanism has an upper and a lower cam portions. The upper cam portion 46, which is not perforated or grooved, is a flat plate-shaped cam for engaging the recess 29 on the main driving shaft 3. The lower cam has a similar shape as that of the cam in FIGS. 8A-8C. The shown body of the adjusting mechanism has five positioning holes, such that a five-level adjustment upon the distances of the bone shaping and cutting tools in the sliding gearbox with respect to the bone shaping and cutting tool in the fixed gearbox is provided.

Figure 13:
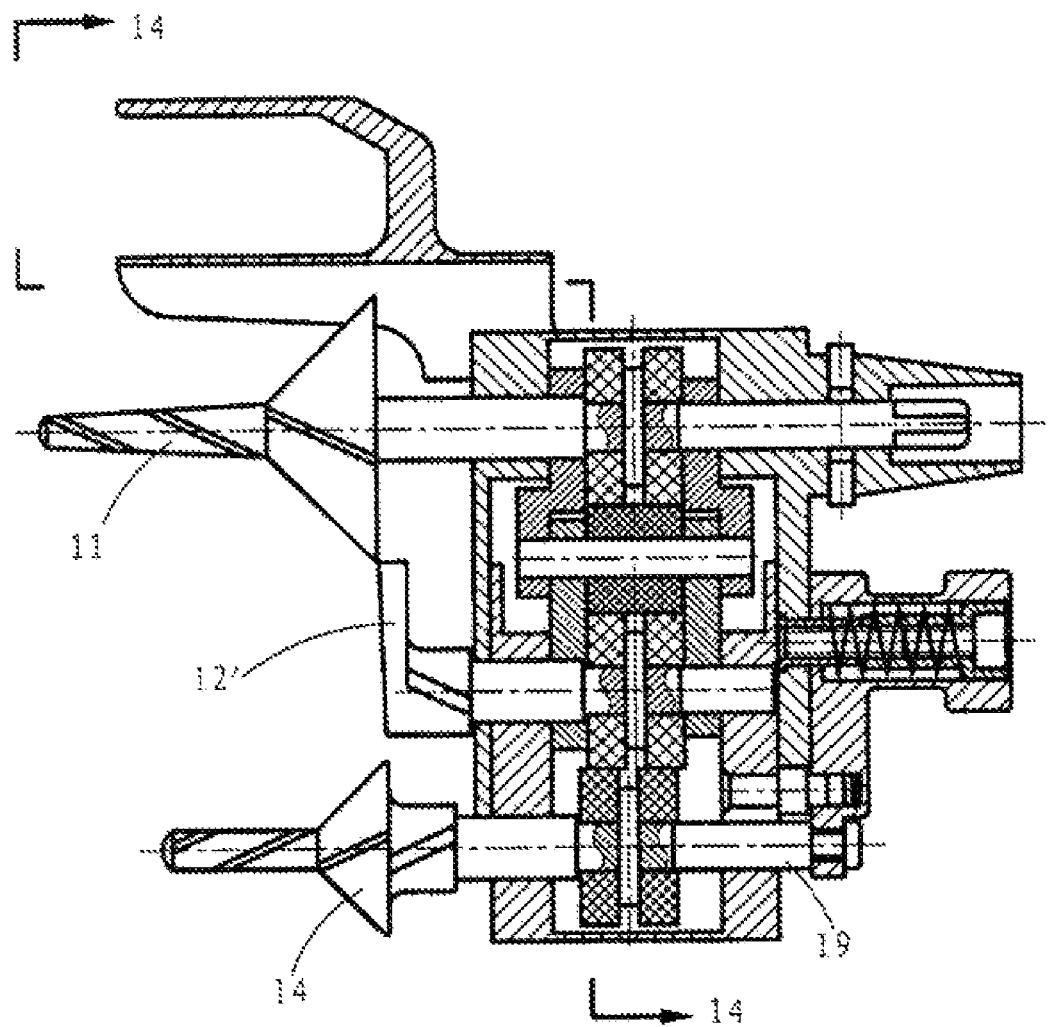
FIG. 13 is a longitudinal sectional view showing a third embodiment of a femoral condyle cutting and shaping device according to the present invention, wherein the adjusting mechanism is located at the fixed position.
Figure 14:
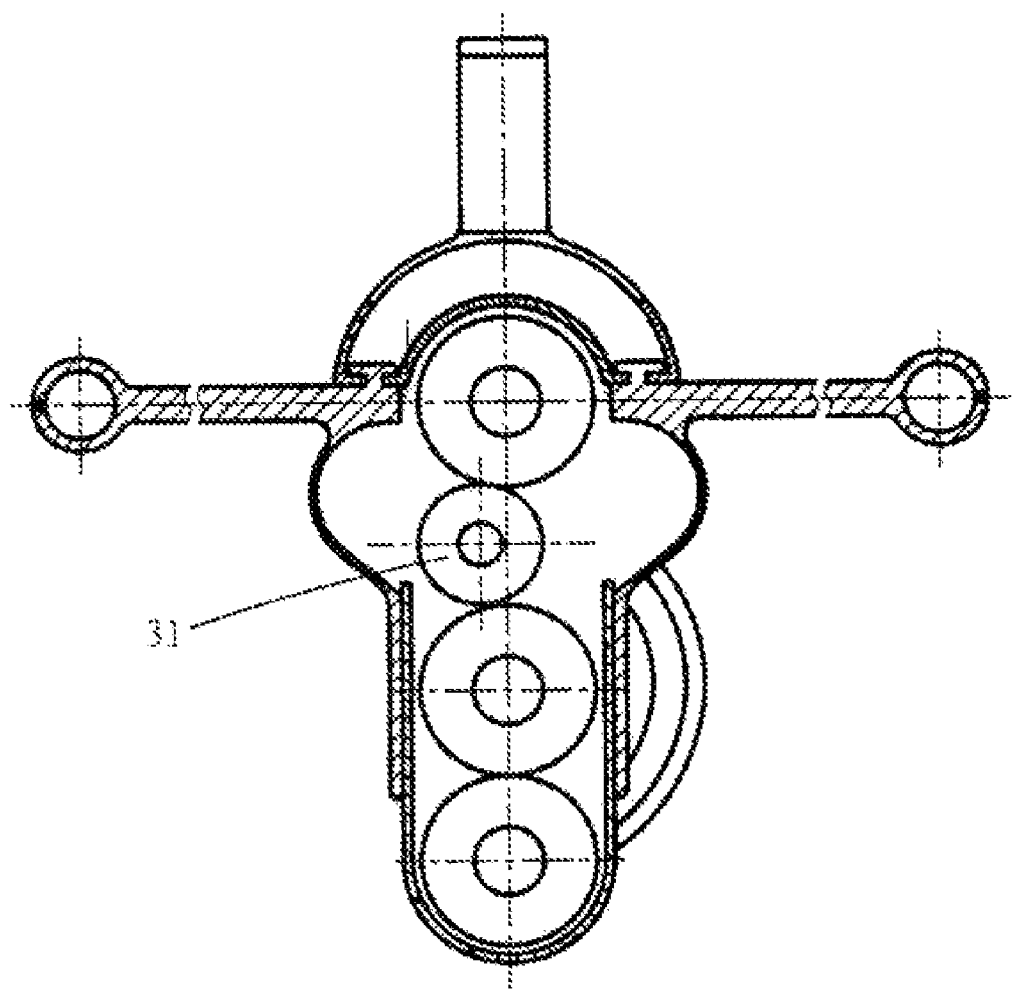
FIG. 14 is a side sectional view showing the third embodiment of the femoral condyle cutting and shaping device according to the present invention along the line 14-14 in FIG. 13.

FIG. 13 is a longitudinal sectional view showing the third embodiment of the femoral condyle cutting and shaping device according to the present invention, with the adjustment mechanism located in its fixed position. FIG. 14 is a side sectional view showing the third embodiment of the femoral condyle cutting and shaping device according to the present invention along the line 14-14 in FIG. 13. The third embodiment as shown in FIGS. 13-14 is substantially same as the first embodiment as shown in FIGS. 6-7, except that only one assistant shaft 31 is provided in the third embodiment to achieve the pivotal rotation between the first connecting member and the second connecting member. In this embodiment, there are only two bone shaping and cutting tools in the sliding gearbox, namely, a second bone shaping and cutting tool 12' in another form (as shown FIG. 25) and a fourth bone shaping and cutting tool 14. In this regard, the body of the adjusting mechanism is connected to the second driven shaft 19 so as to change the relative positions between the first bone shaping and cutting tool 11 and the second and fourth bone shaping and cutting tools 12' and 14 in the sliding gearbox.

Figure 15A:
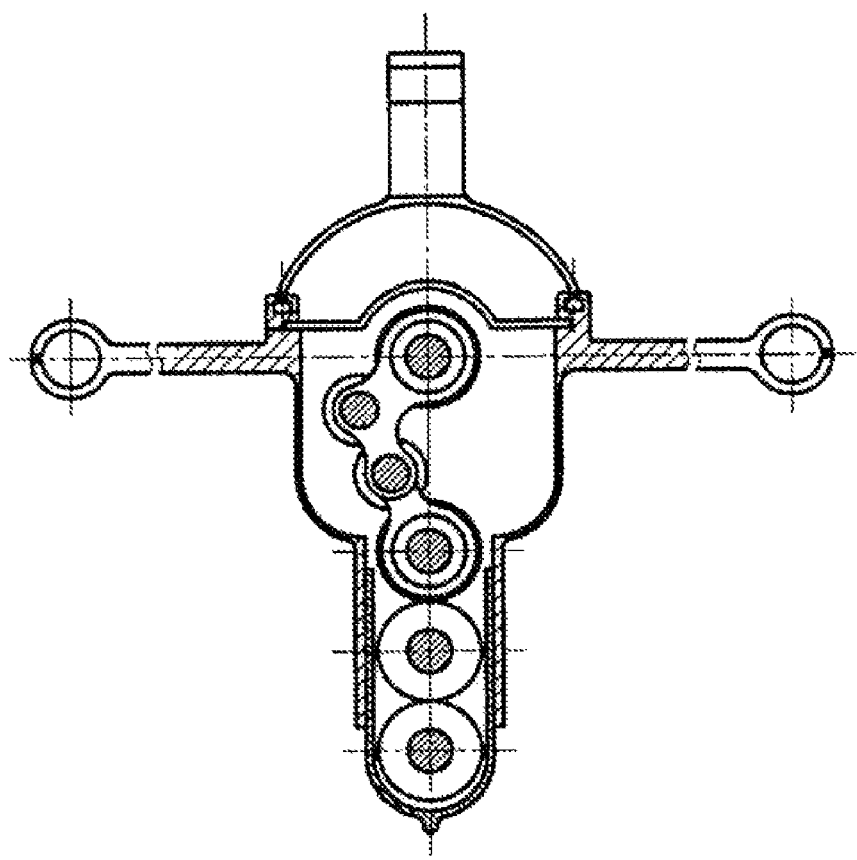
FIG. 15A is a side sectional view showing the first embodiment of the femoral condyle cutting and shaping device according to the present invention when the sliding gearbox is located at the first position.
Figure 15B:
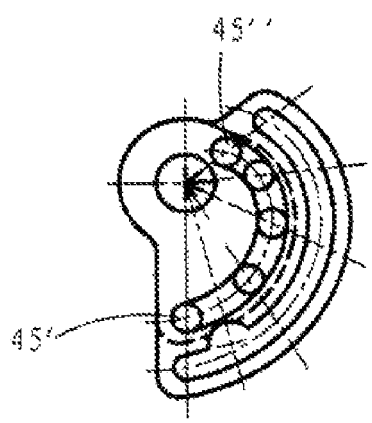
FIG. 15B is a schematic view showing a corresponding position of the cam adjusting mechanism body when the sliding gearbox is located at the first position.

FIG. 15A is a side sectional view showing the first embodiment of the femoral condyle cutting and shaping device according to the present invention when the sliding gearbox is located at the first position. FIG. 15B is a schematic view showing the corresponding position of the cam adjusting mechanism body when the sliding gearbox is located at the first position in FIG. 15A, wherein the positioning pin 21 is inserted into the first positioning hole 45', with the largest pivotal angle between the first connecting member 6 and the second connecting member 9, and the farthest distance from the second, third and fourth bone shaping and cutting tools 12, 13, 14 in the sliding gearbox to the first bone shaping and cutting tool 11 in the fixed gearbox.

Figure 16A:
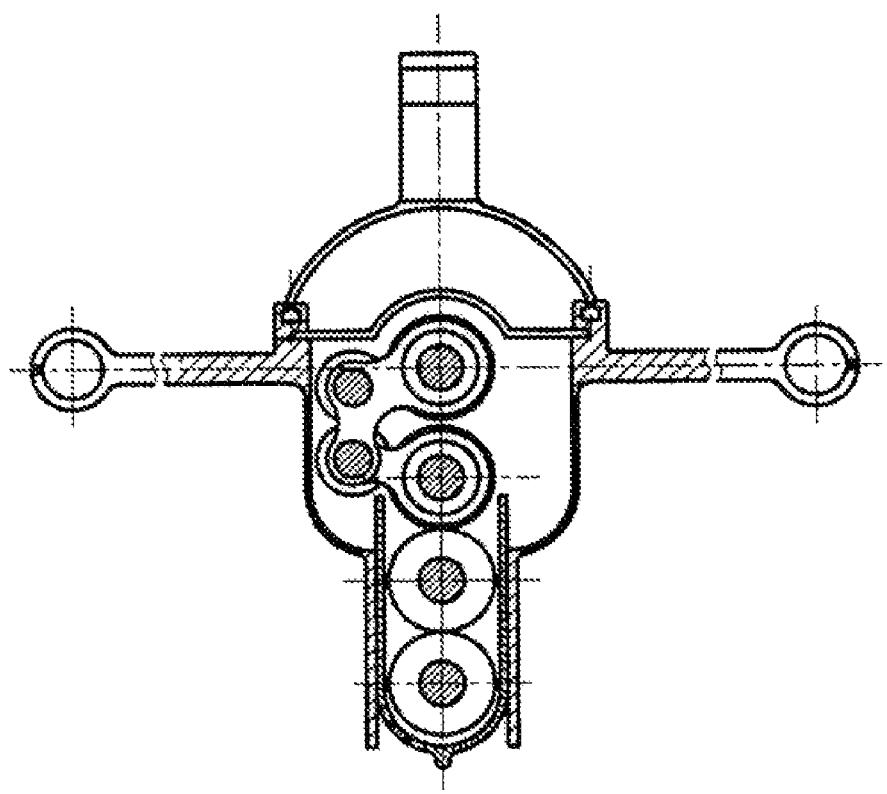
FIG. 16A is a side sectional view showing the first embodiment of the femoral condyle cutting and shaping device according to the present invention when the sliding gearbox is located at a second position.
Figure 16B:
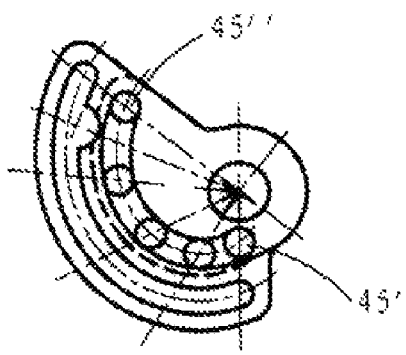
FIG. 16B is a schematic view showing a corresponding position of the cam adjusting mechanism body when the sliding gearbox is located at the second position.

FIG. 16A is a side sectional view showing the first embodiment of the femoral condyle cutting and shaping device according to the present invention when the sliding gearbox is located at the second position. FIG. 16B is a schematic view showing the corresponding position of the cam adjusting mechanism body when the sliding gearbox is located at the second position, wherein the positioning pin is inserted into the fifth positioning hole 45", with the smallest pivotal angle between the first connecting member 6 and the second connecting member 9, and the nearest distance from the second, third and fourth bone shaping and cutting tools 12, 13, 14 in the sliding gearbox to the first bone shaping and cutting tool 11 in the fixed gearbox.

Figure 17B:
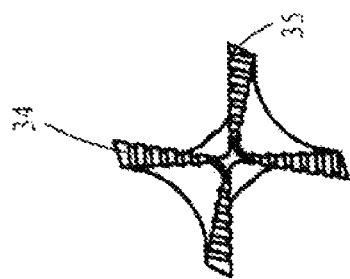
FIG. 17B is a left side view showing the first embodiment of the first bone shaping and cutting tool in FIG. 17A.
Figure 17A:
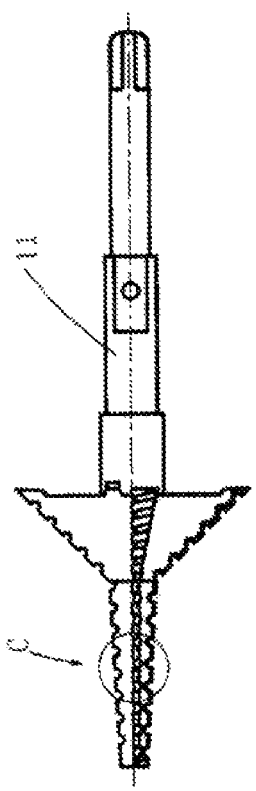
FIG. 17A is a front view showing a first embodiment of a first bone shaping and cutting tool in the first embodiment of the femoral condyle cutting and shaping device according to the present invention.
Figure 17C:
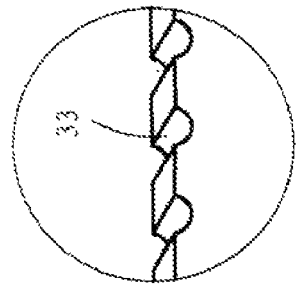
FIG. 17C is a schematic view showing cutting edge chip breaker in the first embodiment of the first bone shaping and cutting tool in FIG. 17A.

FIG. 17A is a front view showing a first example of the first bone shaping and cutting tool in the first embodiment of the femoral condyle cutting and shaping device according to the present invention. FIG. 17B is a left side view showing the first embodiment of the first bone shaping and cutting tool in FIG. 17A. FIG. 17C is a schematic view showing a chip breaker on the cutting edge of the first example of the first bone shaping and cutting tool in FIG. 17A. As can be seen from FIGS. 17A-17C, the first bone shaping and cutting tool 11 has four blades having a straight-sheet-like structure and four cutting edges with two anti-clockwise cutting edges 34 and two clockwise cutting edges 35. As shown in FIG. 17A, each of the blades has two parts. In a first part which is away from one end of the main shaft, each of the blades exhibits a conical shape having a first taper in the blade's width and/or thickness direction. In a second part which is close to said one end of the main shaft, each of the blades exhibits a conical shape having a second taper in the blade's width and/or thickness direction, wherein the second taper is much larger than the first taper. Of course, as a person skilled in the art can understand, the bone shaping and cutting tool 11 may have more than two parts, with the respective parts having different tapers in the blade's width and/or thickness direction. Said tapers can be selected according to practical requirements. Generally speaking, the tapers are usually between 0° to 50°. The blades having cutting edges of different tapers are arranged outside the femoral condyle cutting and shaping device so as to cut two different shaping surfaces at the same time. A design instead of four blades may also be used. For example, the first bone shaping and cutting tool may have less or more than four blades, with both anti-clockwise rotation and clockwise rotation edges, or with only either anti-clockwise rotation or clockwise rotation edges. Blades having a sheet-like structure in a constant thickness may also be used, wherein linear or helical chip breakers 33 can be formed on the edge of each of said blades in a direction approximately perpendicular to the axial direction of the femoral condyle cutting and shaping device, as shown in FIG. 17C. The chip breakers on the blades can be staggered from each other as shown in FIG. 17A.

Figure 18:
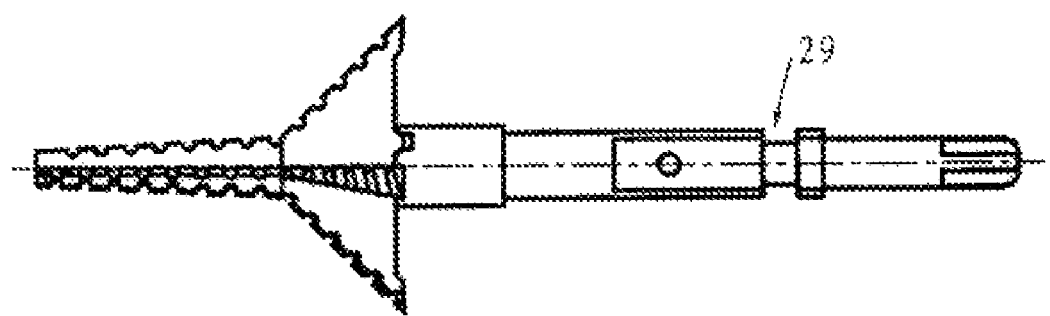
FIG. 18 is a front view showing a second embodiment of a first bone shaping and cutting tool in the femoral condyle cutting and shaping device according to the present invention.

FIG. 18 is a front view showing the first bone shaping and cutting tool in the second embodiment of the femoral condyle cutting and shaping device according to the present invention, wherein the main driving shaft 3 of the first bone shaping and cutting tool is provided with a recess 29.

Figure 20:
FIG. 20 is a left side view showing a second embodiment of the first bone shaping and cutting tool in FIG. 19.
Figure 19:
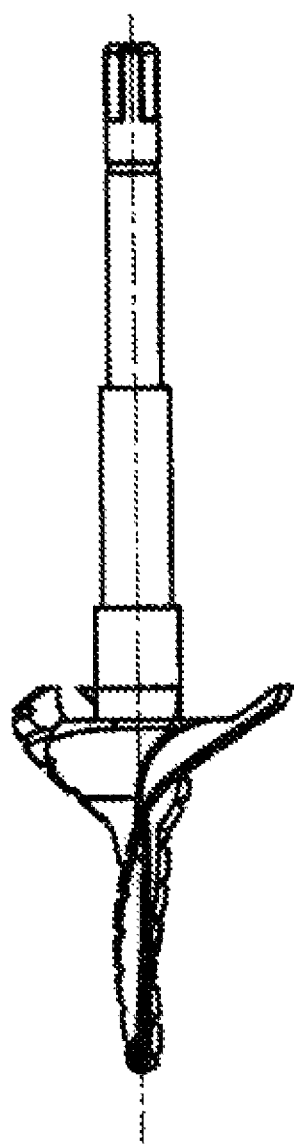
FIG. 19 is a front view showing a second embodiment of a first bone shaping and cutting tool in the first embodiment of the femoral condyle cutting and shaping device according to the present invention.

FIG. 19 is a front view showing a second example of the first bone shaping and cutting tool in the first embodiment of the bone cutting and shaping device according to the present invention. FIG. 20 is a left side view showing the second example of the first bone shaping and cutting tool in FIG. 19. The differences between the shapes of the blades in FIG. 20 from those in FIGS. 18-19 lie in that the bone shaping and cutting tool has three helical blades. Each of the blades has two parts. In a first part, which is away from one end of the main shaft, each of the blades exhibits a conical shape having a first taper in the blade's width and/or thickness direction. On a second part close to one end of the main shall, each of the blades exhibits a conical shape having a second taper in the blade's width and/or thickness direction, wherein the second taper is much larger than the first taper. Of course, as a person skilled in the art can understand, the bone shaping and cutting tool may have more than two parts, with the respective parts having different tapers in the blade's width and/or thickness direction. Said tapers can be selected according to practical requirements. Generally speaking, the tapers are usually between 0° to 50°. The blades having cutting edges of different tapers are arranged outside the femoral condyle cutting and shaping device. A design instead of three blades may also be used. For example, the first bone shaping and cutting tool may have less or more than three blades, or the first bone shaping and cutting tool may has a structure in which the blades are helically shaped and equal in thickness: wherein on the edge of each of the blades, linear or helical chip breakers may be formed in a direction approximately perpendicular to the axial direction of the femoral condyle cutting and shaping device.

Figure 22:
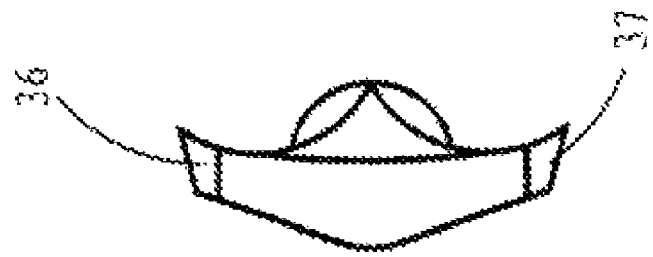
FIG. 22 is a left side view showing an embodiment of the second bone shaping and cutting tool in FIG. 21.
Figure 21:
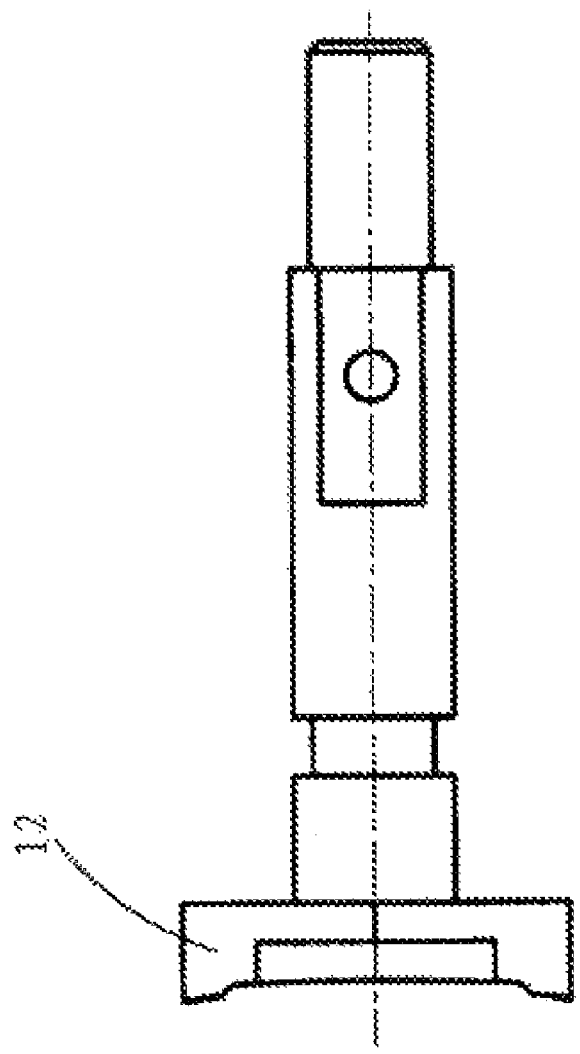
FIG. 21 is a front view showing an embodiment of a second bone shaping and cutting tool in the first embodiment of the femoral condyle cutting and shaping device according to the present invention.

FIG. 21 is a front view showing a first example of the second bone shaping and cutting tool in the first embodiment of the femoral condyle cutting and shaping device according to the present invention. FIG. 22 is a left side view showing the example of the second bone shaping and cutting tool in FIG. 21. Said second bone shaping and cutting tool 12 has two cutting edges, one of which is a anti-clockwise cutting edge 36 and the other of which is a clockwise cutting edge 37.

Figure 24:
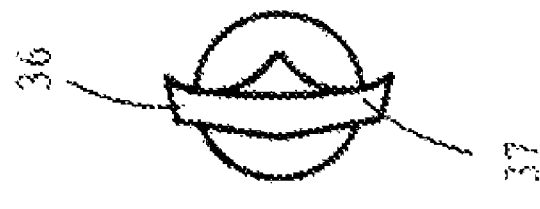
FIG. 24 is a left side view showing an embodiment of the third bone shaping and cutting tool in FIG. 23.
Figure 23:
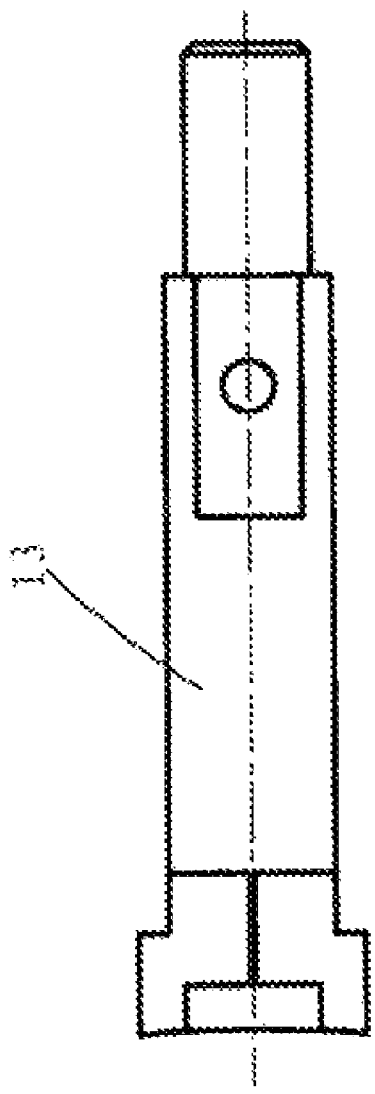
FIG. 23 is a front view showing an embodiment of a third bone shaping and cutting tool in the first embodiment of the femoral condyle cutting and shaping device according to the present invention.

FIG. 23 is a front view showing a first example of the third bone shaping and cutting tool in the first embodiment of the femoral condyle cutting and shaping device according to the present invention. FIG. 24 is a left side view showing the embodiment of the third bone shaping and cutting tool in FIG. 23. The third bone shaping and cutting tool 13 has two cutting edges, one of which is a anti-clockwise cutting edge 36 and the other of which is a clockwise cutting edge 37. The diameter of the third bone shaping and cutting tool 13 is less than that of the second bone shaping and cutting tool 12 in FIGS. 21-22.

Figure 26:
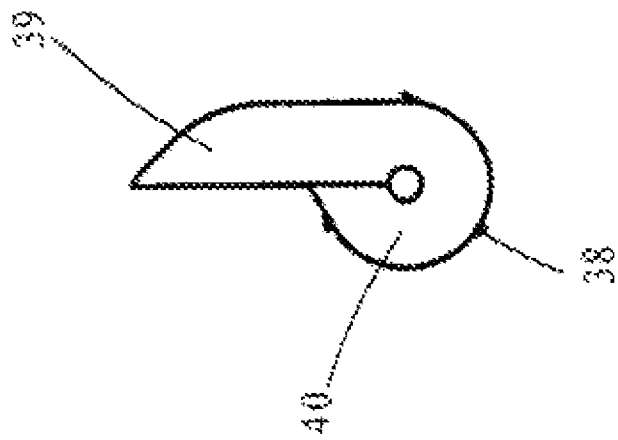
FIG. 26 is a left side view showing an embodiment of the second or the third bone shaping and cutting tool in FIG. 25.
Figure 25:
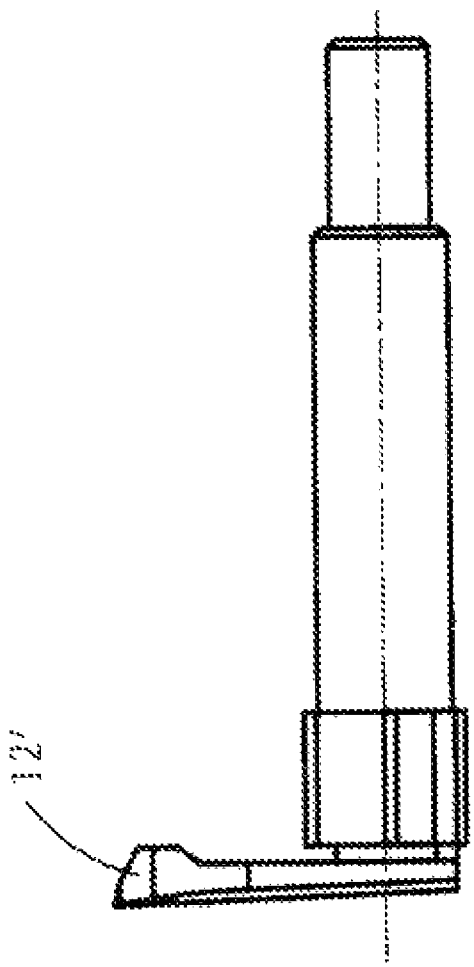
FIG. 25 is a front view showing a second embodiment of the second or third bone shaping and cutting tool in the first embodiment of the femoral condyle cutting and shaping device according to the present invention.

FIG. 25 is a front view of a second example of the second or third bone shaping and cutting tool in the first embodiment of the femoral condyle cutting and shaping device according to the present invention. FIG. 26 is a left side view showing the embodiment of the bone shaping and cutting tool in FIG. 25. The bone shaping and cutting tool, which is a single-blade cutting tool, comprises a blade 39 and three cutting edges 38 formed on a shaft 40 of the tool, a clearance being formed behind each of the cutting edges.

Figure 28:
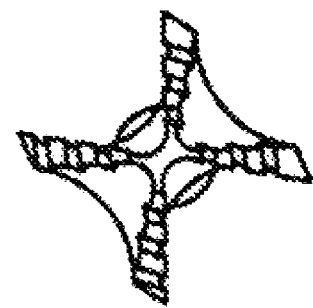
FIG. 28 is a left side view showing an embodiment of the fourth bone shaping and cutting tool in FIG. 27.
Figure 27:
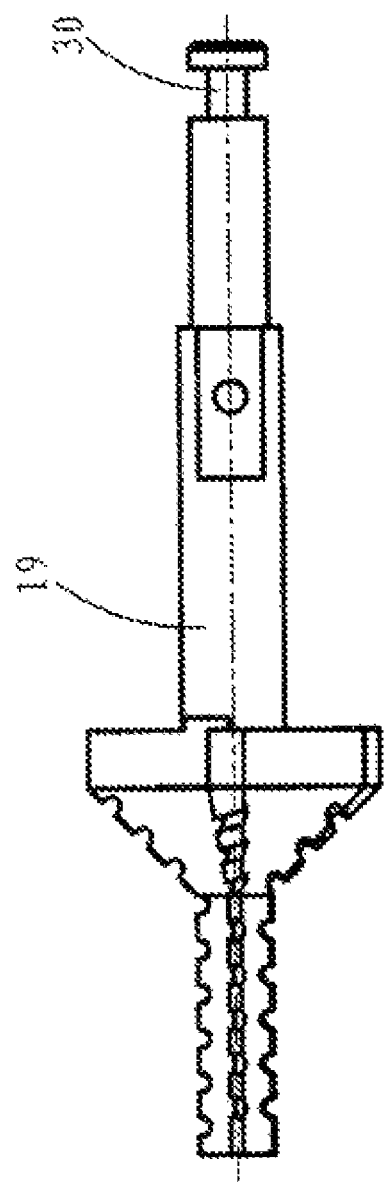
FIG. 27 is a front view showing the embodiment of a fourth bone shaping and cutting tool in the first embodiment of the femoral condyle cutting and shaping device according to the present invention.

FIG. 27 is a front view showing an example of the fourth bone shaping and cutting tool in the first embodiment of the femoral condyle cutting and shaping tool according to the present invention. FIG. 28 is a left side view showing the example of the fourth bone shaping and cutting tool in FIG. 27, wherein a rod-shaped connecting means 30 is formed on the driven shaft 19.

A person skilled in the art could understand that, according to practical requirements, it is possible to dispose only one driven shaft or no less than three driven shafts in the sliding gearbox in the present invention, with a respective bone shaping and cutting tool being mounted correspondingly on each driven shaft. The first to fourth bone shaping and cutting tools and their corresponding driving shafts can be integrally formed, or can be separately formed and subsequently connected in a common manner known by a person skilled in the art. The first to fourth bone shaping and cutting tools are interchangeable if necessary. The first to fourth bone shaping and cutting tools can be fabricated from stainless steel or any other appropriate material.

The above-described embodiments are used for clearly explaining the present invention, instead of limiting the present invention. The protection scope and inspirits of the present invention are defined in the claims of the present invention.

What is claimed is:

1. A femoral condyle cutting and shaping device, comprising:
   a first bone shaping and cutting tool, disposed on an extending end portion of a main driving shaft; and
   a fixed gearbox including the main driving shaft said driving shaft supported on a case of the fixed gearbox, a main driving gear being mounted on the main driving shaft,
   characterized in that,
   the femoral condyle cutting and shaping device further comprises:
   at least one assistant shaft mounted inside the case of the fixed gearbox and at least one assistant gear mounted on said at least one assistant shaft respectively, wherein one of said at least one assistant gear which is adjacent to said main driving gear is engaged with said main driving gear;
   a sliding gearbox including a sliding gearbox case which is capable of being guided to slide in the case of the fixed gearbox, wherein said sliding gearbox includes at least one driven shaft mounted on the sliding gearbox case of the sliding gearbox and at least one driven gear mounted on said at least one driven shaft, wherein one of said at least one driven gear which is adjacent to said at least one assistant gear is engaged with the most adjacent one of said at least one assistant gear, and the axes of said at least one driven shaft and said main driving shaft are parallel to each other;
   a first connecting member and a second connecting member, said assistant shaft being supported on the first connecting member, wherein said first connecting member is supported on said main driving shaft at one end of the first connecting member, the other end of said first connecting member is mounted with one end of said second connecting member onto one of said at least one assistant shaft so as to form a pivotal connection, and the other end of said second connecting member is connected to one of said at least one driven shaft;
   at least one additional bone shaping and cutting tool, mounted on a portion of its corresponding driven shaft which extends outside the sliding gearbox case; and
   an adjusting mechanism arranged outside the case of said fixed gearbox and connected to one of said at least one driven shaft so as to change the relative positions of said first bone shaping and cutting tool and said at least one additional bone shaping and cutting tool.

2. The femoral condyle cutting and shaping device according to claim 1, wherein said at least one assistant shaft comprises a first assistant shaft and a second assistant shaft, and wherein a first assistant gear on the first assistant shaft and a second assistant gear on the second assistant shaft are engaged with each other.

3. The femoral condyle cutting and shaping device according to claim 1, wherein said at least one driven shaft comprises a first driven shaft and a third driven shaft, said first and third driven drafts being engaged with one another.

4. The femoral condyle cutting and shaping device according to claim 1, wherein said at least one driven shaft comprises a first driven shaft, a second driven shaft and a third driven shaft, said first, second and third driven shafts being engaged with one another.

5. The femoral condyle cutting and shaping device according to claim 1, wherein said adjusting mechanism has an adjusting mechanism body with an involute sliding groove formed thereon, and wherein a connecting means that connects said adjusting mechanism with said one of said at least one driven shaft is slidable in the involute sliding groove.

6. The femoral condyle cutting and shaping device according to claim 5, wherein said adjusting mechanism body is provided with a guiding groove for a positioning pin wherein said guiding groove is parallel to the sliding groove and has a plurality of positioning recesses therein, and wherein said positioning holes cooperate with the positioning pin as attached to the sliding gearbox case, so as to fix the respective bone shaping and cutting tools.

7. The femoral condyle cutting and shaping device according to claim 6, wherein said plurality of positioning recesses have different depths.

8. The femoral condyle cutting and shaping device according to any one of claims 5 to 7, wherein the adjusting mechanism body further includes a flat plate-shaped cam portion that engages with a recess on the main driving shaft.

9. The femoral condyle cutting and shaping device according to claim 5, wherein said adjusting mechanism comprises a screw disposed in an opening of the adjusting mechanism body and connected to the case of the fixed gearbox, and a compression spring surrounding said screw.

10. The femoral condyle cutting and shaping device according to claim 5, wherein said connecting means that connects said adjusting mechanism and said one driven shaft is a portion of said driven shaft.

11. The femoral condyle cutting and shaping device according to claim 5, wherein said connecting means that connects said adjusting mechanism and said one of said at least one driven shaft is a rod that is connected to said driven shaft.

12. The femoral condyle cutting and shaping device according to claim 1, further comprising two positioning guide plates that are arranged on the two opposite sides of the case of said fixed gearbox, respectively, each of said positioning guide plates being provided with a handle at an end thereof; a protective shield that is arranged on said fixed gearbox case to surround the first bone shaping and cutting tool; and another positioning guide plate that is provided on said protective shield.

13. The femoral condyle cutting and shaping device according to claim 1, wherein each of the bone shaping and cutting tools comprises a plurality of blades each having a straight-sheet-like structure.

14. The femoral condyle cutting and shaping device according to claim 13, wherein each of the blades has a flat plate-shaped structure of constant thickness.

15. The femoral condyle cutting and shaping device according to claim 13, wherein each of the blades further has a conical shape at the end proximal to the corresponding shaft having at least one taper in the blade's width and thickness directions.

16. The femoral condyle cutting and shaping device according to claim 1, wherein the bone shaping and cutting tools each comprises a plurality of blades each having a helical structure.

17. The femoral condyle cutting and shaping device according to claim 16, wherein each of the blades has a helical plate-shaped structure of constant thickness.

18. The femoral condyle cutting and shaping device according to claim 16, wherein each of the blades further has a conical shape at the end proximal to the corresponding shaft having at least one taper in the blade's width and thickness directions.

19. The femoral condyle cutting and shaping device according to claim 13 or 16, wherein the edge of each of the blades is provided with helical chip breakers.

20. The femoral condyle cutting and shaping device according to claim 13 or 16, wherein the edge of each of the blades is provided with linear chip breakers formed in a direction perpendicular to an axial direction of the femoral condyle cutting and shaping device.

21. The femoral condyle cutting and shaping device according to claim 13 or 16, wherein the cutting edges of the blade include anti-clockwise cutting edges 22. The femoral condyle cutting and shaping device according to claim 13 or 16, wherein the cutting edges of the blade include clockwise cutting edges.

23. The femoral condyle cutting and shaping device according to claim 1, wherein said bone shaping and cutting tool is a single-blade cutting tool, and comprises a blade and three cutting edges formed on a shaft of the tool, a clearance being formed behind each of the cutting edges.

* * * * *